(12) United States Patent
Li et al.

(10) Patent No.: US 11,314,375 B2
(45) Date of Patent: Apr. 26, 2022

(54) MULTICHANNEL PRESSURE CONTROL SYSTEM WITH USER FRIENDLY INTERFACE

(71) Applicant: Precigenome, LLC, San Jose, CA (US)

(72) Inventors: Chen Li, Sunnyvale, CA (US);
Yunfeng Ling, San Jose, CA (US);
Cifeng Fang, Redmond, WA (US);
Yaqi Wang, San Jose, CA (US); Yu Liu, San Jose, CA (US)

(73) Assignee: Precigenome, LLC, San Jose, CA (US)

( * ) Notice: Subject to any disclaimer, the term of this patent is extended or adjusted under 35 U.S.C. 154(b) by 0 days.

(21) Appl. No.: 16/587,899

(22) Filed: Sep. 30, 2019

(65) Prior Publication Data

US 2020/0104029 A1 Apr. 2, 2020

Related U.S. Application Data

(60) Provisional application No. 62/739,751, filed on Oct. 1, 2018.

(51) Int. Cl.
| | |
|---|---|
| *G06F 3/04815* | (2022.01) |
| *G06F 3/0488* | (2022.01) |
| *A61M 5/34* | (2006.01) |
| *G06F 3/04842* | (2022.01) |

(52) U.S. Cl.
CPC ......... *G06F 3/04815* (2013.01); *A61M 5/348* (2013.01); *G06F 3/0488* (2013.01); *G06F 3/04842* (2013.01); *A61M 2205/3331* (2013.01); *A61M 2205/505* (2013.01)

(58) Field of Classification Search
CPC .... H04B 7/2041; H04W 16/28; H04W 72/04; H04W 84/06; A61M 2205/3331; A61M 2205/505; A61M 5/348; A61M 5/14212; A61M 1/1611; A61M 5/1723; A61M 1/0035; A61M 16/22; A61M 1/0001; A61M 5/1408; A61M 1/3644; G06F 3/04815; G06F 3/04842; G06F 3/04847; G06F 3/0488; B01L 3/5027; C12M 29/04; G06Q 50/24; A61G 7/05715; G01N 1/31; G01N 21/59
See application file for complete search history.

(56) References Cited

U.S. PATENT DOCUMENTS

| | | |
|---|---|---|
| 3,797,516 A | 3/1974 | Forster et al. |
| 4,923,008 A | 5/1990 | Wachowicz et al. |
| 5,163,909 A | 11/1992 | Stewart |
| 7,763,211 B2 | 7/2010 | Rinderknecht et al. |
| 8,122,901 B2 | 2/2012 | Zeng et al. |

(Continued)

*Primary Examiner* — Richard J Hong
(74) *Attorney, Agent, or Firm* — Umberg Zipser LLP; Jason Tejani

(57) ABSTRACT

Disclosed herein are pressure control systems, comprising: a touch screen electrically connected to industrial computer or embedded operating system; a pressure output channel connected to the touch screen and/or the industrial computer or embedded operating system; and pressure control unit for communicating with the pressure output channel, wherein the pressure control unit can be controlled with the touch screen, and wherein the industrial computer or embedded operating system comprises preinstalled software with User Interface (UI) for pressure control setup and running the system.

16 Claims, 5 Drawing Sheets

(56) References Cited

U.S. PATENT DOCUMENTS

| | | | |
|---|---|---|---|
| 9,127,361 B2 | 9/2015 | Ding | |
| 2005/0059926 A1 | 3/2005 | Sage et al. | |
| 2005/0256444 A1* | 11/2005 | O'Mahony | G06Q 50/24 604/5.02 |
| 2008/0060700 A1 | 3/2008 | Gharib et al. | |
| 2009/0257886 A1 | 10/2009 | Rosenstein et al. | |
| 2010/0174270 A1* | 7/2010 | Charlez | A61M 1/0035 604/540 |
| 2011/0017667 A1* | 1/2011 | Delmage | A61M 1/1611 210/646 |
| 2011/0224523 A1* | 9/2011 | Budiman | A61M 5/1723 600/365 |
| 2011/0253224 A1* | 10/2011 | Linder | G01N 21/59 137/2 |
| 2012/0329142 A1 | 12/2012 | Battrell et al. | |
| 2013/0094996 A1* | 4/2013 | Janssenswillen | A61M 1/3644 422/45 |
| 2014/0038166 A1* | 2/2014 | Linder | B01L 3/5027 435/3 |
| 2014/0069539 A1* | 3/2014 | Bi | A61M 16/22 137/625 |
| 2014/0208251 A1* | 7/2014 | Houde | A61M 5/1408 715/771 |
| 2015/0025482 A1* | 1/2015 | Begin | A61M 1/0001 604/318 |
| 2015/0175950 A1* | 6/2015 | Hirschel | C12M 29/04 435/239 |
| 2015/0268668 A1 | 9/2015 | Nahmias et al. | |
| 2016/0022520 A1* | 1/2016 | Streeter | A61G 7/05715 5/655.3 |
| 2016/0187363 A1* | 6/2016 | Kim | B01L 3/5027 435/3 |
| 2016/0339423 A1 | 11/2016 | Quake et al. | |
| 2017/0095810 A1 | 4/2017 | Li et al. | |
| 2017/0348731 A1 | 12/2017 | Hoefler et al. | |
| 2018/0132990 A1* | 5/2018 | Baeten | A61M 5/14212 |
| 2018/0200483 A1* | 7/2018 | Laby | A61M 25/005 |
| 2020/0332243 A1* | 10/2020 | Dadgar | G01N 1/31 |

\* cited by examiner

MULTICHANNEL PRESSURE CONTROL SYSTEM WITH USER FRIENDLY INTERFACE

This application claims priority to U.S. Provisional Application No. 62/739,751, filed Oct. 1, 2018, which is herein incorporated by reference in its entirety.

FIELD OF THE INVENTION

The field of the invention is pressure pump and medical devices.

BACKGROUND

The following description includes information that may be useful in understanding the present invention. It is not an admission that any of the information provided herein is prior art or relevant to the presently claimed invention, or that any publication specifically or implicitly referenced is prior art.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

High precision pressure control technology has been widely used in different fields, such as microfluidic flow control, biotechnology, chemical detection etc. However in the current market pressure control systems can only provide single preset pressure or a flow rate output. In the few cases where independent control of multiple pressure lines has been disclosed, such systems can only be used by advanced users and are not user-friendly.

For example, the Elveflow® line of products enables independent control of four pressure lines. However these products require advanced users having programming knowledge, and further requires a few weeks to a few months to achieve such control. Similarly, Fluigent® OEM line of products enables the control of up to 8 pressure lines. However, such a control over the fluid is performed by utilizing one or more controllers that are entirely separate from the processor which collects and processes data from the (one or more) sensors that are used.

US20150268668A1 by Nahmias et al discloses an apparatus for controlling a microfluidic circuit. The device is adapted to centrally operate and control an operation of various microfluidic circuits. The apparatus disclosed by Nahmias et al carries out control, data collection, and analysis by a single microprocessor. However, the system requires an experienced and advanced user to control and optimize the different algorithms of the system, such as, multiple hill climbing algorithms, and genetic algorithms.

Thus, there remains a need in the art for new devices and systems that enables independent control of several pressure lines, while also providing a user-friendly system.

SUMMARY OF THE INVENTION

The inventive subject matter provides a pressure control system with an interface design which allows users to set pressure and duration using touch screen. Users can also set more complicated time dependent multi-channel pressure control. All the settings can be done using touch screen without connecting external computers. The system can also connect external systems for triggering pressure control.

In one aspect, disclosed herein is a pressure control system, comprising: a touch screen electrically connected to industrial computer or embedded operating system; a pressure output channel connected to the touch screen and/or the industrial computer or embedded operating system; and pressure control unit for communicating with the pressure output channel, wherein the pressure control unit can be controlled with the touch screen, and wherein the industrial computer or embedded operating system comprises preinstalled software configured to present a User Interface (UI) on the touch screen or other display for pressure control setup and running the system.

Also disclosed herein is a method of using a pressure control system, comprising: providing a pressure control system comprising a touch screen electrically connected to industrial computer, a pressure output channel connected to the touch screen and/or the industrial computer or embedded operating system; and pressure control unit for communicating with the pressure output channel, wherein the pressure control units can be controlled with the touch screen, and wherein the industrial computer or embedded operating system comprises preinstalled software with User Interface (UI) for pressure control setup and running the system; and using the pressure control system by starting the pressure control unit using the touch screen.

Various objects, features, aspects and advantages of the inventive subject matter will become more apparent from the following detailed description of preferred embodiments, along with the accompanying drawing figures in which like numerals represent like components.

DETAILED DESCRIPTION

The instant subject matter is directed towards a pressure control system, comprising: a touch screen electrically connected to industrial computer or embedded operating system; a pressure output channel connected to the touch screen and/or the industrial computer or embedded operating system; and pressure control unit for communicating with the pressure output channel, wherein the pressure control unit can be controlled with the touch screen, and wherein the industrial computer or embedded operating system comprises preinstalled software configured to present a User Interface (UI) on the touch screen or other display for pressure control setup and running the system.

The system provided herein has several advantages over the currently available pressure control systems. Most of the pressure control systems currently available only provide single preset pressure or a flow rate output. In the few cases where independent control of multiple pressure lines has been disclosed, such systems can only be used by advanced users and are not user-friendly. Thus, there remains a need in the art for new devices and systems that enables independent control of several pressure lines, while also providing a user-friendly system.

Figure 1:
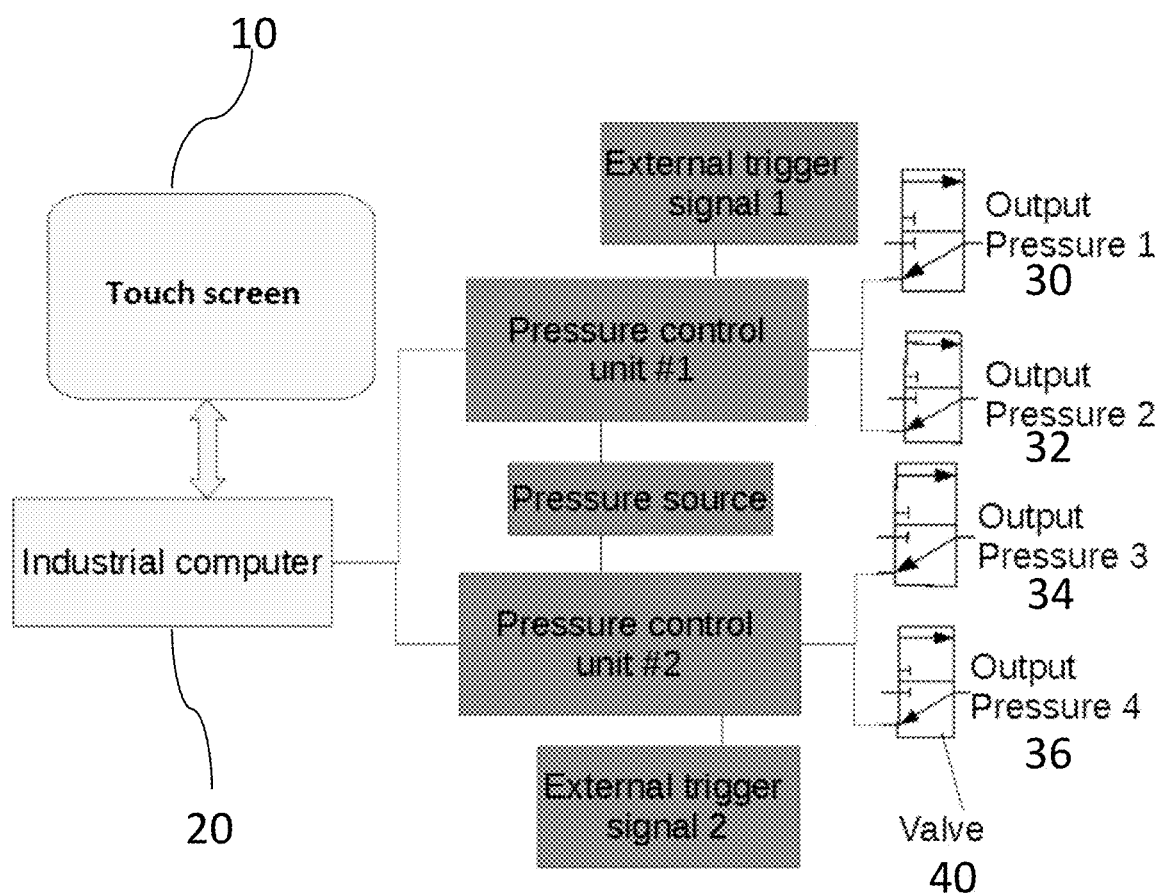
FIG. 1 illustrates, in accordance with the embodiments herein, a schematic of the system architecture.
Figure 2:
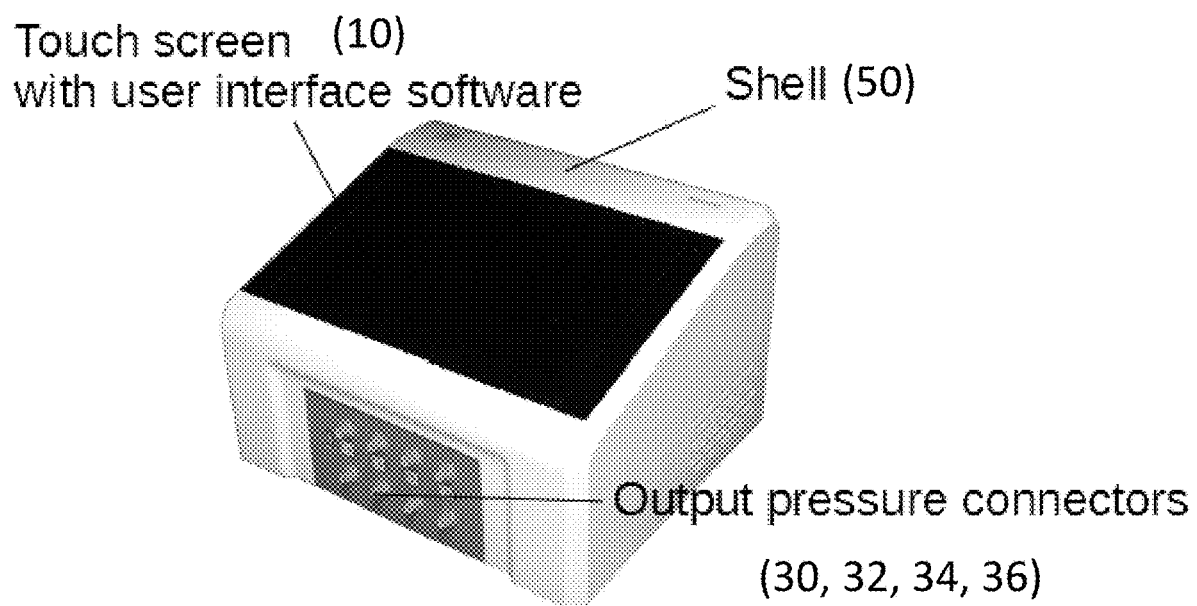
FIG. 2 illustrates, in accordance with the embodiments herein, an appearance of the pressure control system.

One embodiment of the pressure control system disclosed herein is shown schematically in FIG. 1. It includes an industrial computer or embedded operating system 20, a touch screen 10, pressure sources (e.g. pump) (25, 27), pressure control units (30, 32, 34, 36), and 3-way valves module 40. FIG. 2 shows another embodiment of the pressure control system disclosed herein, and includes a touch screen 10, shell 50, and output pressure channel connections (30, 32, 34, 36). The touch screen is connected with the industrial computer (or embedded operating system) through video cables. Touch screen displays system control user interface. The industrial computer or embedded operating system runs system control and UI software, sends user operation parameters to pressure control units, and receives status data from the pressure control units and sensor data. FIG. 1 illustrates two pressure control units and four output pressure channels. In other embodiments, pressure control units and output pressure channels may be extended to multiples. Thus, the system is also contemplated to comprise multiple pressure control units and/or multiple pressure output interfaces.

The touch screen user interface is an integral part of the system disclosed herein. The UI provides pressure and duration setting for each pressure output channel. Furthermore, the UI may provide pressure on and off setting for each pressure output channel. The UI is further contemplated to provide real time monitoring of pressure for each pressure output channel graphically and numerically. In some embodiments, UI may provide scripting option for time dependent multichannel pressure and flow setting.

The pressure control system may further comprise proportional valves, pressure sensor and/or control feedback loop that are used to achieve pressure control. USB, RS232, CAN bus, Digital I/O, and Ethernet connection may be provided for data transfer and communication. The pressure output interface is contemplated to be Luer lock or Luer slip fitting. The pressure control system may be portable.

The pressure control system disclosed herein may be useful in several industries, for example the presently disclosed pressure control system may be used in biological and/or chemical applications. In particular, the pressure control system may be used to dispense liquids or detect chemicals. The disclosed pressure control system may be incorporated in a medical device or coupled with a microfluidic application.

The instant disclosure also provides a method of using a pressure control system, comprising: providing a pressure control system comprising a touch screen electrically connected to industrial computer or embedded operating system, a pressure output channel connected to the touch screen and/or the industrial computer or embedded operating system; and pressure control unit for communicating with the pressure output channel, wherein the pressure control units can be controlled with the touch screen, and wherein the industrial computer or embedded operating system comprises preinstalled software with User Interface (UI) for pressure control setup and running the system; and using the pressure control system by starting the pressure control unit using the touch screen.

Pressure sources can be internal (e.g. pumps) and/or external (e.g. compressed air). Users can choose which pressure source is used through UI. Pressure sources are connected with inlets of pressure control module. Pressure is adjusted by proportional valves based on pressure sensor data and user's setting. Output of pressure control unit is connected to 3-way valves. Through controlling 3-way valves, the system can control on and off for each channel.

Figure 3:
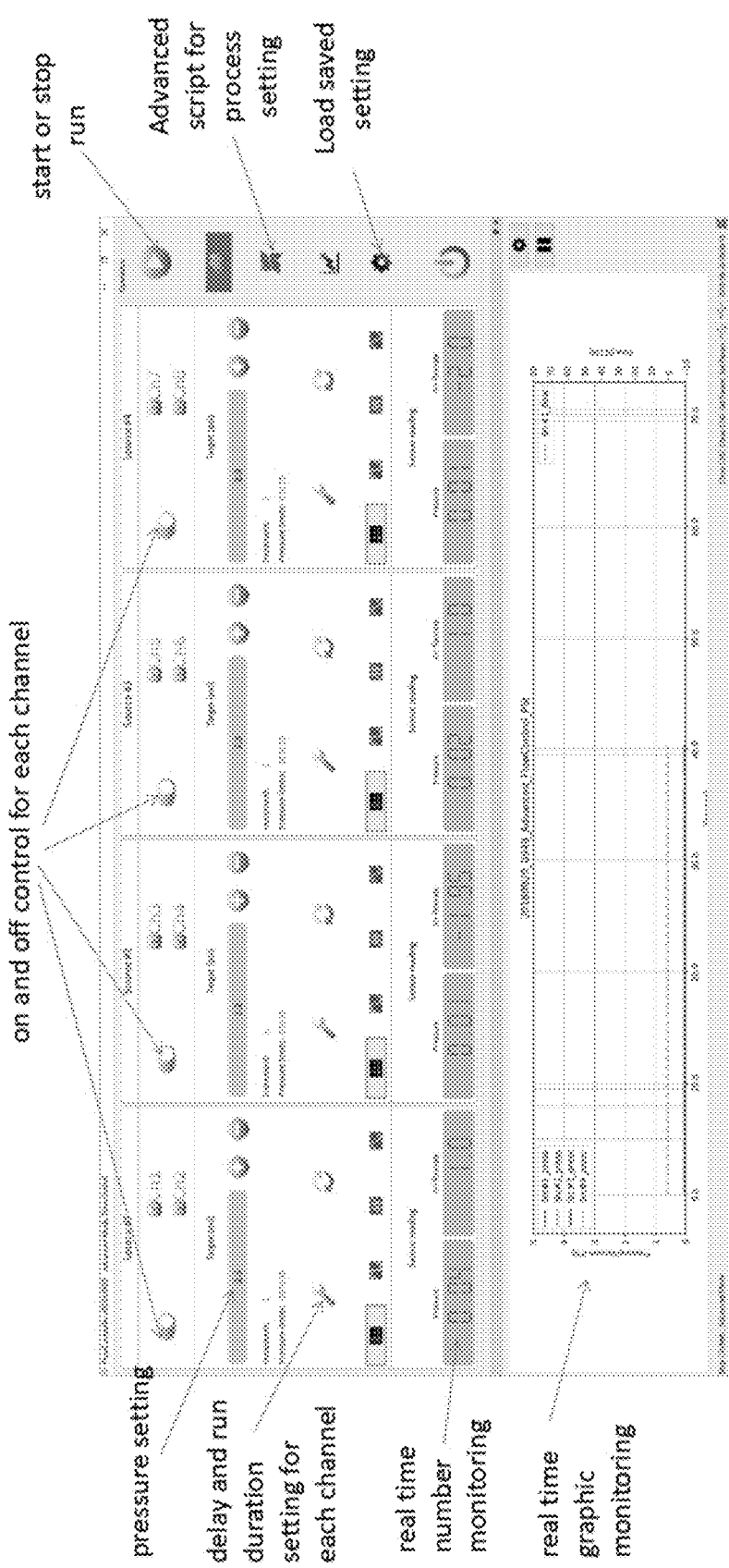
FIG. 3 illustrates, in accordance with the embodiments herein, an example of the software display that provides an easy to use User Interface (UI) for quick set-up.
Figure 4:
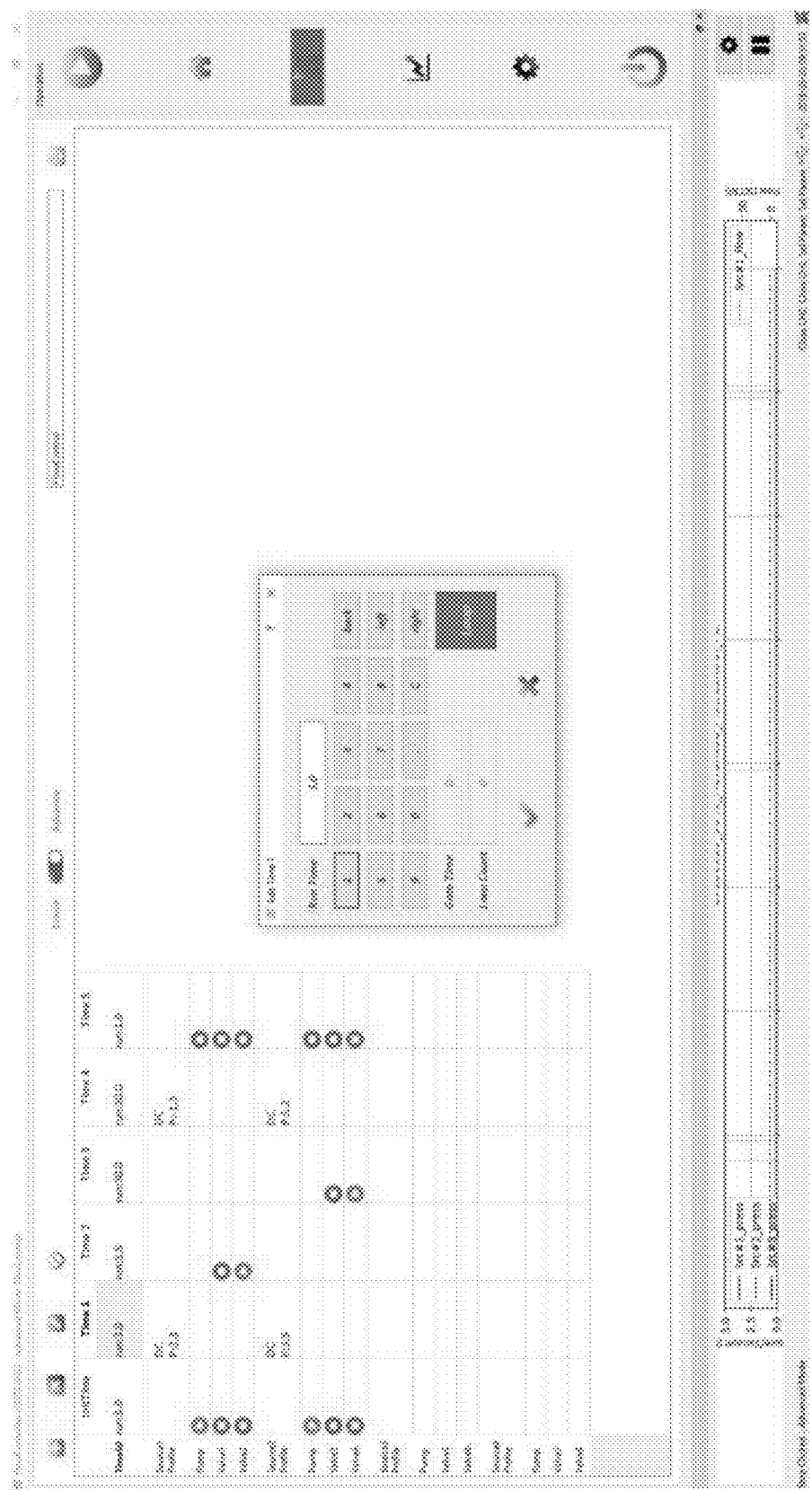
FIG. 4 illustrates, in accordance with the embodiments herein, an example of a more advanced set-up UI for process control.
Figure 5:
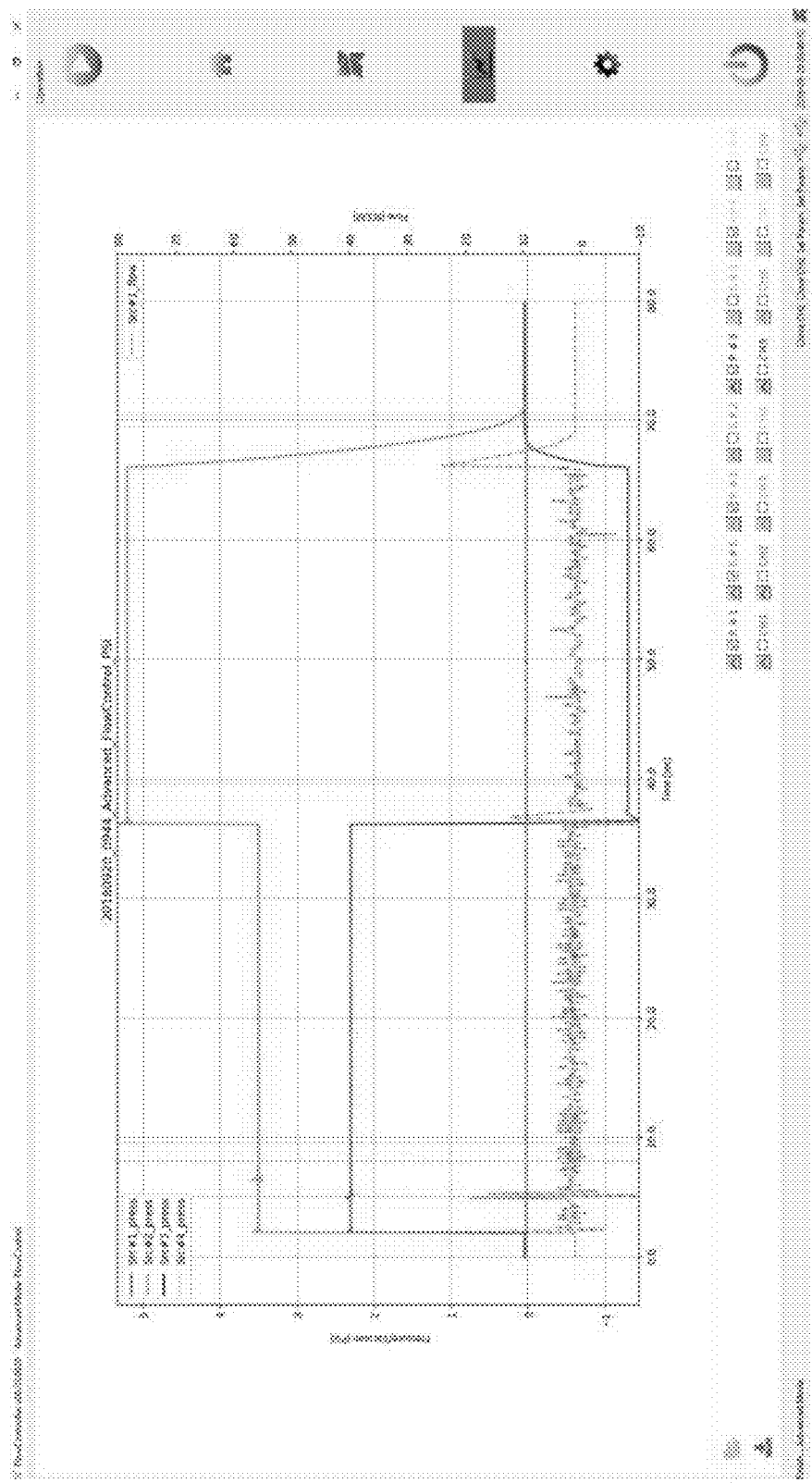
FIG. 5 illustrates, in accordance with the embodiments herein, real time pressure and flow monitoring.

Users can achieve quick setup of pressure, duration, and on and off for each channel through UI on touch screen as shown in FIG. 3. By one click, users can run pressure control system based on its setting. Users can also achieve more advanced setting by clicking advanced setting button. The setup UI is shown in FIG. 4. Users can achieve more complicated time dependent pressure control for each channel. For example, at t0 the system starts initialization and controls each channel to preset pressure. At t1, valve 1 and 3 are opened and channel 1 and 3 are connected to external source to provide preset pressures. At t2, the pressure setting for channel 1 and 3 are changed to different pressures. The control system quickly adjusts the pressures for channel 1 and 3 and output different pressures. The whole process can also be monitored real time by system provided UI as shown in FIG. 5. Complicated process control setting can also be saved and loaded through UI.

In some embodiments, the numbers expressing quantities of time, ingredients, properties such as pressure, number of valves, output and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A microfluidic pressure control system for providing pneumatic pressure to an external device, comprising:
   a) an outer shell;
   b) a touch screen electrically connected to an embedded operating system;
   c) first and second microfluidic pressure output channels connected to the touch screen and capable of providing pneumatic pressures to an external device;
   d) a first pressure control unit and a second pressure control unit that, independently, control the pneumatic pressures provided to the external device by the first and second microfluidic pressure output channels, respectively; and
   e) a Digital I/O connection;
   wherein each of (a)-(e) are operatively connected with each other,
   wherein the outer shell comprises an outer surface comprising the touch screen and comprises the first and second microfluidic pressure output channels and the first and second pressure control units therein,
   wherein the embedded operating system comprises preinstalled software with User Interface (UI) for setting up the pressure control unit, running the pressure control system, and communicating with the external device through the Digital I/O connection,
   wherein the first pressure control unit is connected to a first pressure source and the second pressure control unit is connected to a second pressure source,
   wherein the first pressure control unit comprises a first 3-way valve and the second pressure control unit comprises a second 3-way valve for turning the first and second microfluidic pressure output channels on and off, respectively,
   wherein the first and second pressure control units are controlled by the UI through the touch screen, and
   wherein the UI comprises real time monitoring of the pneumatic pressures for the first and second microfluidic pressure output channels and status of the external device through the Digital I/O connection.

2. The pressure control system of claim 1, wherein each of the first and second pressure control units comprises a pressure output interface.

3. The pressure control system of claim 2, wherein each of the first and second pressure output interfaces comprises a Luer lock or Luer slip fitting.

4. The pressure control system of claim 1, wherein the UI comprises scripting for setting time-dependent control of the first and second pressure output channels, flow setting, and the Digital I/O, RS232, and/or CAN bus connection, and wherein the scripting comprises pressure and duration setting for each of the first and second pressure output channels.

5. The pressure control system of claim 1, wherein proportional valves, pressure sensor and control feedback loop are used to achieve pressure control.

6. The pressure control system of claim 1, wherein USB, RS232, CAN bus, and Ethernet connection are provided for data transfer and communication.

7. The pressure control system of claim 1, wherein the pressure control system is portable.

8. The pressure control system of claim 1, wherein the pressure control system is for dispensing liquid or chemical detection utilizing the external device.

9. The pressure control system of claim 1, wherein the pressure control system is for a microfluidic application utilizing the external device.

10. A method of using the pressure control system of claim 1, the method comprising:
    providing a pressure control system comprising the touch screen electrically connected to the embedded operating system, the first and second pressure output channels connected to the touch screen or the embedded operating system; and the first and second pressure control units for communicating with the first and second pressure output channels, respectively, wherein the first and second pressure control units can be controlled with the touch screen, and wherein the embedded operating system comprises preinstalled software with User Interface (UI) for pressure control setup and running the system;
    providing an external device capable of receiving pneumatic pressures from the first and second pressure output channels; and
    using the pressure control system by starting the first and second pressure control units using the touch screen.

11. The method of claim 10, wherein the pressure control system comprises multiple pressure output interfaces.

12. The method of claim 10, wherein each of the at least one pressure control units outputs a different pressure.

13. The method of claim 10, wherein the external device comprises a medical device.

14. The method of claim 10, wherein the method is for microfluidic application utilizing the external device.

15. The method of claim 10, wherein the method is for dispensing liquids utilizing the external device.

16. The method of claim 10, wherein the method is for detecting chemicals utilizing the external device.

* * * * *